United States Patent
Willingham et al.

[11] Patent Number: 5,853,463
[45] Date of Patent: Dec. 29, 1998

[54] MARINE ANTIFOULING AGENT

[75] Inventors: Gary Lewis Willingham, Glenside; Linda Marguerite Oltman, Collegeville, both of Pa.

[73] Assignee: Rohm and Haas Company, Phila., Pa.

[21] Appl. No.: 108,767

[22] Filed: Jul. 1, 1998

Related U.S. Application Data

[60] Provisional application No. 60/051,870 Jul. 7, 1997.

[51] Int. Cl.⁶ .............................. C09D 5/16; H01N 31/00
[52] U.S. Cl. ................ 106/18.35; 106/18.3; 106/18.32; 106/18.33; 106/18.34; 106/18.36; 424/78.09; 424/635; 424/638; 424/646; 424/650; 514/64; 514/241; 514/277; 514/365; 514/479; 514/493; 514/494; 514/596; 514/600; 514/646; 514/678; 514/711; 523/122; 523/179
[58] Field of Search ............................... 514/678, 64, 241, 514/277, 365, 479, 493, 494, 596, 600, 646, 711, 741; 424/78.09, 635, 638, 646, 650; 106/15.05, 18.3, 18.32, 18.33, 18.34, 18.35, 18.36; 523/122, 179

[56] References Cited

U.S. PATENT DOCUMENTS 5,071,479 12/1991 Gruening ............................... 106/18.32

FOREIGN PATENT DOCUMENTS

SHO 63-2243   1/1988   Japan .............................. A01N 61/00

OTHER PUBLICATIONS

"Convenient Preparation of Unsymmetrically Substituted Benzils by Permanganate Oxidation of B–Oxo Phosphorus Ylides"; R. Alan Aitken, J.I.G. Cadogan and Ian Gosney; Phosphorus, Sulfur, and Silcon, 1995, vol. 101, pp. 281–286.
"Synthesis of new derivatives of benzil", Krieg, Benno; Chem. Ber. (1969), 102(1), 371–3 No month.
Chemical Abstract No. 14:86502 which is an abstract of an article by Aitken et al entitled "Convenient Preparation of . . . Ylides", Phosphorus, Sulfur Silicon Relat. Elem. (1995), 101(1–4), 281–6, 1995 no month.
Chemical Abstract No. 125:152218 which is an abstract of an article by McHale et al entitled "Solubility Of Benzil . . . Solvent Mixtures", J. Chem. Eng. Data (1996), 41(5), 1184–1186, 1996 no month.

*Primary Examiner*—Anthony Green
*Attorney, Agent, or Firm*—S. Matthew Cairns

[57] ABSTRACT

Disclosed is a method of inhibiting the growth of marine organisms on a marine structure, by applying diphenyldiones. These compounds may be directly incorporated into the marine structure during manufacture, directly applied to the structure, or applied to the structure by means of a coating.

9 Claims, No Drawings

MARINE ANTIFOULING AGENT

This is a nonprovisional application of prior pending provisional application Ser. No. 60/051,870 filed Jul. 7, 1997.

BACKGROUND OF THE INVENTION

This invention relates generally to a method of inhibiting the growth of organisms on a marine structure. In particular, this invention relates to the use of diphenyldiones as marine antifouling agents.

Marine antifouling agents are used commercially to prevent growth of organisms on marine structures. Tributyltin oxide and other organotins have been the major marine antifouling agents in use for many years. There is currently much concern over the effects of tin on marine environments. For example, high levels of tin in harbor waters have been linked to shell deformation in some bivalve species, such as oysters.

Some organic compounds have been suggested as marine antifouling agents. For example, U.S. Pat. No. 5,071,479 (Gruening) discloses the use of 3-iodopropargyl N-butyl carbamate as a marine antifouling agent. These types of compounds have not achieved commercial prominence because they do not meet the same performance requirements as tin-based antifouling agents.

JP 88 002 243 B (Yoshino et al.) discloses a broad list of classes of compounds having an absorbance in the 380 nm to 800 nm wavelength region as marine antifouling agents. Among the classes of compounds disclosed are aromatic ketones, which are exemplified by compounds having fused ring structures, such as anthraquinone and substituted anthraquinones. These compounds also do not meet the same performance requirements as tin-based antifouling agents.

There is a continuing need for marine antifouling agents having increased performance and little or no harmful effects on marine environments.

STATEMENT OF THE INVENTION

The present invention provides a method of inhibiting the growth of marine organisms on a marine structure, comprising applying to, on, or in a marine structure, article, or composition in contact with or intended for contact with sea or brackish water an effective amount of a diphenyldione marine antifouling agent of the formula:

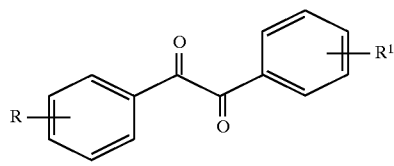

(I)

wherein R and $R^1$ are independently selected from H, $(C_1-C_{20})$alkyl and halo$(C_1-C_{20})$alkyl.

DETAILED DESCRIPTION OF THE INVENTION

As used herein, "marine antifouling agents" include algaecides and molluscicides. "Marine antifoulant activity" is intended to include both the elimination of and inhibition or prevention of growth of marine organisms. Marine organisms controlled by the marine antifouling agents suitable for use in this invention include both hard and soft fouling organisms. Generally speaking, the term "soft fouling organisms" refers to plants and invertebrates, such as slime, algae, kelp, soft corals, tunicates, hydroids, sponges, and anemones and the term "hard fouling organisms" refers to invertebrates having some type of hard outer shell, such as barnacles, tubeworms and molluscs.

The term "alkyl" means straight chain, branched, cyclic, or any combination thereof The terms "halogen" and "halo" mean fluorine, chlorine, bromine, or iodine. All amounts are percent by weight ("%wt"), unless otherwise noted, and all %wt ranges are inclusive. As used herein, the following abbreviations are applied: mL=milliliter, $\mu$L=microliter, g=grams, $\mu$g/mL=micrograms per milliliter, ppm=parts per million, mm=millimeter, nm=nanometer, $\mu$m=micrometer, DMSO=dimethyl sulfoxide, and ASTM=American Society for Testing and Materials.

The compounds useful as marine antifouling agents are those of formula (I), above. Preferred compounds are those wherein R and $R^1$ are independently selected from H, $(C_1-C_8)$alkyl and halo$(C_1-C_8)$alkyl. Especially preferred are the compounds wherein R and $R^1$ are independently selected from H and methyl.

The compounds of the present invention are generally commercially available or may be prepared by methods known in the literature. For example, Aitken et al., *Phosphorus, Sulfur Silicon Relat. Elem.*, 101, 281–6 (1995) and Krieg, *Chem. Ber.*, 102, 371–3 (1969) disclose the preparation of various diphenyldiketones and are herein incorporated by reference to the extent they teach how to make the compounds of the present invention.

The marine antifouling agents of the present invention can be used to inhibit the growth of marine organisms by application of an effective amount of one or more of the marine antifouling agents onto or into a marine structure. Depending upon the particular marine structure to be protected, the marine antifouling agents of the present invention can be directly incorporated into the marine structure, applied directly to the marine structure, or incorporated into a coating which is then applied to the marine structure.

Suitable structures include, but are not limited to: boats, ships, oil platforms, piers, pilings, docks, elastomeric rubbers, and fish nets. The marine antifouling agents of the present invention are typically directly incorporated into structures such as elastomeric rubber or fish net fibers during manufacture. Direct application of the compounds of the invention is typically made to structures such as fish nets or wood pilings. The compounds of the invention can also be incorporated into a marine coating, such as a marine paint or varnish.

In general, the amount of marine antifouling agent necessary to inhibit or prevent the growth of marine organisms is 0.1 to 30 %wt based on the weight of the structure to be protected or based on the weight of the coating to be applied. When the marine antifouling agents of the invention are directly incorporated into or directly applied onto a structure, the amount of the antifouling agent suitable to inhibit the growth of marine organisms is generally 0.1 to 30 %wt based on the weight of the structure. It is preferred to use an amount 0.5 to 20 %wt; more preferably, 1 to 15 %wt. When incorporated into a coating, the amount of marine antifouling agent suitable to inhibit the growth of marine organisms is generally 0.1 to 30 %wt based on the weight of said coating. The amount of marine antifouling agent is preferably 0.5 to 15 %wt; more preferably, 1 to 10 %wt.

If one of the marine antifouling agents of the invention is to be combined with a second marine antifouling agent, the weight ratio of the first marine antifouling agent to the second marine antifouling agent is 99:1 to 1:99; preferably, 75:25 to 25:75. The total of the combined marine antifouling agents necessary to inhibit or prevent the growth of marine organisms is generally 0.1 to 30 %wt based on the weight of the structure to be protected or the weight of the coating to be applied, depending on the application.

In general, the marine antifouling agents of the invention are incorporated in a carrier such as water; organic solvent, such as xylene, methyl isobutyl ketone, and methyl isoamyl ketone; or mixtures thereof.

Direct applications of the marine antifouling agents of the invention may be by any conventional means, such as dipping, spraying, or coating. Fish nets, for example, may be also protected by dipping the fish nets into a composition comprising one or more of the compounds of the invention and a carrier or by spraying the fish nets with said composition.

Structures such as wood pilings and fish nets may be protected by directly incorporating the marine antifouling agents into the structure For example, a composition comprising one or more marine antifouling agents in a carrier may be applied to wood used for pilings by means of pressure treatment or vacuum impregnation. These compositions may also be incorporated into a fish net fiber during manufacture.

Marine coatings typically comprise a binder, solvent, and other optional ingredients. The solvent may be either organic solvent, water or mixtures thereof. The marine antifouling agents of the invention are suitable for use in both solvent and water based marine coatings. Solvent based marine coatings are preferred.

Any conventional binder may be utilized in the marine antifouling coating incorporating one or more of the antifouling agents of the invention. Suitable binders include, but are not limited to: polyvinyl chloride in a solvent based system; chlorinated rubber in a solvent based system; acrylic resins in solvent based or aqueous systems; vinyl chloride-vinyl acetate copolymer systems as aqueous dispersions or solvent based systems; butadiene-styrene rubbers; butadiene-acrylonitrile rubbers; butadiene-styrene-acrylonitrile rubbers; drying oils such as linseed oil; asphalt; epoxies; siloxanes; and the like.

The marine coatings of the present invention may optionally contain one or more of the following: inorganic pigments, organic pigments, or dyes, and natural resins, such as rosin. Water based coatings may also optionally contain: coalescents, dispersants, surface active agents, rheology modifiers, or adhesion promoters. Solvent based coatings may also optionally contain extenders, plasticizers, or rheology modifiers.

Marine coating compositions of the present invention typically comprise 2 to 20 %wt binders, up to 15 %wt rosins/modified rosins, 0.5 to 5 %wt plasticizers, 0.1 to 2 %wt antisettling agent, 5 to 60 %wt solvent/diluent, up to 70 %wt cuprous oxide, up to 30 %wt pigments (other than cuprous oxide), and up to 30 %wt marine antifouling agent.

Marine antifouling coatings of the present invention may be applied to a structure to be protected by any of a number of conventional means. Suitable means of application include, but are not limited to, spraying; rolling; brushing; or dipping.

It is known in the art that the performance of marine antifouling agents may be enhanced by combination with one or more other marine antifouling agents. Thus, other known marine antifouling agents may be combined advantageously with the marine antifouling agents of this invention. The compounds of this invention may be combined with, e.g., tin based marine antifoulants. Such a combination has the advantage of reducing the amount of tin used and thereby lessening the amount of tin in the environment. Other marine antifouling agents useful in combination with the compounds of the invention include, but are not limited to: manganese ethylenebisdithiocarbamate; cuprous oxide; zinc dimethyl dithiocarbamate; 2-methylthio-4-t-butylamino-6-cyclopropylamino-s-triazine; 2,4,5,6-tetrachloroisophthalonitrile; 3-(3,4-dichlorophenyl)-1,1-dimethylurea; zinc ethylenebisdithiocarbamate; copper thiocyanate; 4,5-dichloro-2-n-octyl-3-isothiazolone; N-(fluorodichloromethylthio)-phthalimide; N,N-dimethyl-N'-phenyl-N'-fluorodichloromethylthio-sulfamide; zinc 2-pyridinethiol-1-oxide; tetramethylthiuram disulfide; copper-10% nickel alloy solid solution; 2,4,6-trichlorophenylmaleimide; 2,3,5,6-tetrachloro-4-(methylsulfonyl)-pyridine; 3-iodo-2-propynyl butyl carbamate; diiodomethyl p-tolyl sulfone; bis dimethyl dithiocarbamoyl zinc ethylenebisdithiocarbamate; phenyl (bispyridil) bismuth dichloride; 2-(4-thiazolyl)-benzimidazole; pyridine triphenyl borane; phenylamides; halopropargyl compounds; or 2-haloalkoxyaryl-3-isothiazolones. Suitable 2-haloalkoxyaryl-3-isothiazolones include, but are not limited to: 2-(4-trifluoromethoxyphenyl)-3-isothiazolone, 2-(4-trifluoromethoxyphenyl)-5-chloro-3-isothiazolone, and 2-(4-trifluoromethoxyphenyl)-4,5-dichloro-3-isothiazolone.

The following examples are presented to illustrate further various aspects of the present invention, but are not intended to limit the scope of the invention in any aspect.

EXAMPLE 1

Tests were conducted to determine the toxicity of the marine antifouling agents of the present invention to Dunaliella. Dunaliella are indicative of soft fouling organisms.

The effectiveness of the marine antifouling agents of the present invention and 3-iodopropargyl N-butyl carbamate (Comparative) against *Dunaliella parva* were determined by a twofold serial dilution procedure which determined the Minimum Inhibitory Concentration ("MIC") of test compound required to inhibit the growth of an algal inoculum. McLachlan's Medium (prepared according to J. McLachlan, "The Culture of *Dunaliella Tertiolecta* Butcher—A Euryhaline Organism", *Canadian Journal of Microbiology, volume* 6, 1960) was used for maintaining cultures and performing the tests. Tests were carried out in 96-well, round bottom tissue culture plates. All incubation was done at 23° C. (±2° C).

Cultures were grown in 50 mL of medium contained in 250 mL baffle flasks with silicone sponge closures (Bellco Glass, Vineland, N.J., #2004-00004, 28 mm), on a rotary shaker under constant cool white illumination. Log phase cultures (4–7 days old) were used in testing. The culture was standardized to an absorbance of 0.1 at 490 nm by addition of fresh medium. The standardized culture was then diluted with an equal volume of fresh medium. The inoculated medium was dispensed into a 96 well plate, using an eight channel microliter pipettor. Each well in Column 1 received 195 $\mu$L; all the other wells received 100 $\mu$L.

Solutions of test compound at 40x the highest concentration to be tested were prepared in an appropriate solvent. A single channel microliter pipettor was used to deliver 5 $\mu$L of the compound solution to three replicate wells of Column 1. Two wells in Column 1 received no compound solution and were used as reference growth control wells. The eight-channel pipettor was used to mix the contents of Column 1 by drawing up and dispensing back to the wells a 100 μL volume. This was repeated 3–4 times, then 100 μL from the wells in Column 1 was transferred to Column 2. The mixing and transferring process was continued through Column 12, with the excess 100 μl from the well in Column 2 discarded. The plates were covered with plastic tissue culture lids, placed inside plastic bags with zipper seals, and placed under fluorescent lights to incubate for one week. At the end of that time, the plates were examined for growth, as evidenced by easily visible green color, using a mirrored microplate reader.

Wells showing growth comparable to that in the untreated control wells were rated as "+", and wells having no growth were given a rating of "0", and wells that had only slight growth were rated "±". Results were recorded as the median of the three replicate results and are reported below as the minimum concentration to inhibit growth (MIC).

| Activity Against *Dunaliella parva* | |
|---|---|
| Compound | MIC (ppm) |
| R=R$^1$=H | 0.6 |
| Comparative | 6.2 |

Compounds showing activity against Duniella at less than 1 ppm are considered to have high activity against soft fouling organisms. These results demonstrate the compounds of this invention are more efficacious against soft fouling organisms than known antifouling agents.

EXAMPLE 2

Tests were conducted to determine the toxicity of the marine antifouling agents of the present invention to Artemia. Artemia are indicative of hard fouling organisms.

Substitute ocean water was prepared following ASTM Method D 1141-90. The water was sterilized by filtration through a 0.22 micron cellulose acetate membrane filter. San Francisco Bay Brand® (San Francisco Bay Brand, Inc., Newark, Calif.) *Artemia satlina* cysts were purchased from a local aquarium supply store. The cysts were hatched in a 250 mL Erlenmeyer flask. The Artemia cysts (0.2 g) were weighed into a sterilized flask. One hundred mL of sterile ASTM sea water was added to the flask. The flask was placed on an orbital shaker set at approximately 150 rotations per minute and 28° C. After 24 hours, the contents of the flask were poured into a separatory funnel. The egg shells were separated from the Artemia nauplii (larvae), as the shells floated to the top. The nauplii were returned to the flask for another 24 hours shaking. The inoculum was prepared by pouring the nauplii into a crystallizing dish 48 hours after the cysts were originally placed on the shaker. After the nauplii congregated, they were taken up in a sterile serological pipette and transferred into another crystallizing dish. The suspension was stirred with a magnetic stirrer enough to keep the nauplii in suspension. Eighty mL of sterile sea water was added to the suspension. Using an eight channel microliter pipetter loaded with wide bore pipette tips, 100 μL of the suspension was transferred into a column of a 96 well, flat bottom, tissue culture plate. The number of nauplii in 3 to 4 wells was counted under a microscope. The number was averaged, and the inoculum was adjusted through further dilution, to 25 to 30 nauplii per 100 mL.

Stock solutions of the compounds to be tested, including 3-iodopropargyl N-butyl carbamate (Comparative), were prepared on a weight to volume basis. Stock solutions were prepared at 40 times the highest concentration to be tested. Solvents were chosen based on the solubility of the compound to be tested. Solvents used were DMSO, acetone, or isopropanol. The solvents were tested to make sure that they had no effect on the test results.

Ninety six well, flat bottom, tissue culture plates were used for these tests. One hundred ninety μL of sterile ASTM sea water was added to column 1 of each plate. One hundred μL of sterile ASTM sea water was added to columns 2 through 12 of each plate. Ten μL of a stock solution of one compound to be tested was added to the first three wells of column 1. The next 2 wells were skipped, as they served as untreated controls. Ten μL of a stock solution of a second compound to be tested was added to the last three wells of column 1. Serial dilutions were performed by mixing and transferring 100 μL from column 1 to column 2, then from column 2 to 3, and the process was continued until all 12 columns were diluted. One hundred μL from column 12 was discarded. One hundred μL of the stirring Artemia inoculum was added to each well of the plate. The test plate was covered with a plastic tissue culture plate lid and incubated for 24 hours at 25° C.

Plates were read under a low magnification microscope 24 and 48 hours after the nauplii were added to the plate. The highest dilution in which all of the nauplii are dead is the LC$_{100}$. Nauplii are considered alive if any movement is seen during the viewing period. Results of this test are shown in the following table.

| Artemia LC$_{100}$ (ppm) | |
|---|---|
| Compound | 24 Hours |
| R=R$^1$=H | 12.5 |
| Comparative | 25 |

Compounds showing activity against Artemia at 5–25 ppm are considered to have moderate activity against hard fouling organisms. These results demonstrate that the compounds of this invention are more efficacious against hard fouling organisms than known antifouling agents.

What is claimed is:

1. A method of inhibiting the growth of marine organisms on a marine structure, article, or composition in contact with or intended for contact with sea or brackish water comprising applying to, on, or in such marine structure a marine organism inhibiting amount of a diphenyldione marine antifouling agent of formula:

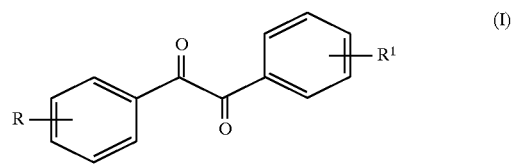

wherein R and R$^1$ are independently selected from H, (C$_1$–C$_{20}$)alkyl and halo(C$_1$–C$_{20}$)alkyl.

2. The method of claim 1 wherein R and R$^1$ are selected from H, (C$_1$–C$_8$)alkyl and halo(C$_1$–C$_8$)alkyl.

3. The method of claim 2 wherein R and R$^1$ are independently selected from H and methyl.

4. The method of claim 1 wherein the marine antifouling agent is incorporated in a carrier or marine coating.

5. The method of claim 4 wherein the amount of the marine antifouling agent in the carrier or coating is from 0.1 to 30 %wt based on the weight of the structure to be protected or based on the weight of the coating to be applied.

6. The method of claim 1 wherein the marine structure is selected from the group consisting of boats, oil platforms, piers, pilings, docks, and fish nets.

7. A method of inhibiting the growth of marine organisms on a marine structure, article, or composition in contact with or intended for contact with sea or brackish water comprising applying to, on, or in such marine structure a marine organism inhibiting amount of a combination of a diphenyldione marine antifouling agent of formula:

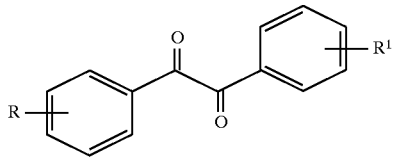
(I)

wherein R and $R^1$ are independently selected from $H(C_1-C_{20})$alkyl and halo$(C_1-C_{20})$alkyl and a second marine antifouling agent selected from the group consisting of; tin based marine antifoulants; manganese ethylenebisdithiocarbamate; cuprous oxide; zinc dimethyl dithiocarbamate; 2-methylthio-4-t-butylamino-6-cyclopropylamino-s-triazine; 2,4,5,6-tetrachloroisophthalonitrile; 3-(3,4-dichlorophenyl)-1,1-dimethylurea; zinc ethylenebisdithiocarbamate; copper thiocyanate; 4,5-dichloro-2-n-octyl-3-isothiazolone; N-(fluorodichloromethylthio)-phthalimide; N,N-dimethyl-N'-phenyl-N'-fluorodichloromethylthiosulfamide; zinc 2-pyridinethiol-1-oxide; tetramethylthiuram disulfide; copper-10% nickel alloy solid solution; 2,4,6-trichlorophenylmaleimide; 2,3,5,6-tetrachloro-4-(methylsulfonyl)-pyridine; 3-iodo-2-propynyl butyl carbamate; diiodomethyl p-tolyl sulfone; bis dimethyl dithiocarbamoyl zinc ethylenebisdithiocarbamate; phenyl (bispyridil) bismuth dichloride; 2-(4-thiazolyl)-benzinmidazole; pyridine triphenyl borane; and 2-haloalkoxyaryl-3-isothiazolones is applied to, on or in the marine structure; wherein the ratio of the diphenyldione marine antifouling agent to the second marine antifouling agent is from 99:1 to 1:99.

8. A marine antifouling coating composition comprising a marine antifouling agent of the formula

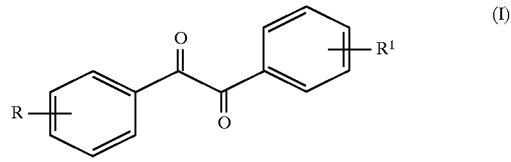
(I)

wherein R and $R^1$ are independently selected from H, $(C_1-C_{20})$alkyl and halo$(C_1-C_{20})$alkyl; and a carrier selected from the group consisting of water, organic solvent, and mixtures thereof.

9. The composition of claim 8 wherein R and $R^1$ are selected from H, $(C_1-C_8)$alkyl and halo$(C_1-C_8)$alkyl.

* * * * *